(12) United States Patent
Lee et al.

(10) Patent No.: US 10,948,482 B2
(45) Date of Patent: Mar. 16, 2021

(54) METHOD FOR CANCER GRADING

(71) Applicant: NATIONAL SYNCHROTRON RADIATION RESEARCH CENTER, Hsinchu (TW)

(72) Inventors: Yao-Chang Lee, Hsinchu (TW); Pei-Yu Huang, Hsinchu (TW)

(73) Assignee: NATIONAL SYNCHROTRON RADIATION RESEARCH CENTER, Hsinchu (TW)

( * ) Notice: Subject to any disclaimer, the term of this patent is extended or adjusted under 35 U.S.C. 154(b) by 136 days.

(21) Appl. No.: 16/002,538

(22) Filed: Jun. 7, 2018

(65) Prior Publication Data
US 2019/0376953 A1   Dec. 12, 2019

(51) Int. Cl.
*G01N 33/50* (2006.01)

(52) U.S. Cl.
CPC ..... *G01N 33/5091* (2013.01); *G01N 2800/56* (2013.01)

(58) Field of Classification Search
CPC .................. G01N 33/5091; G01N 2800/56
See application file for complete search history.

(56) References Cited

FOREIGN PATENT DOCUMENTS

JP       2012-21830 A       2/2012

OTHER PUBLICATIONS

Lee, Y., "Biomedical Applications of Synchrotron-based Infrared Microspectroscopy at NSRRC/ Fast Sceening and Grading of Cancer", 129 pages.
Lee, Y., et al., "Biomedical Application of Synchrotron-based Infrared Microspectroscopy at NSRRC", 1 pages.
Lee, Y., et al., "Early Detection of Cancer by using Wax Physisorption Kinetic and FTIR imaging", 2 pages.
Lee, C., et al., "Arsentite Regulates Prolongation Glycan Residues of Membrane Glycoprotein: A pivotal Study via Wax Physisorption Kinetics and FTIR Imaging", 13 pages.
European Patent Office. Search Report, dated Sep. 18, 2018. 8 pages.
EP Office Action dated Mar. 8, 2019, issued in corresponding EP Patent Application No. 18 179 385.2, 4 pages.
Office Action issued in corresponding JP Application No. 2019-106214, dated Jun. 16, 2020.

*Primary Examiner* — Teresa E Knight
(74) *Attorney, Agent, or Firm* — Muncy, Geissler, Olds & Lowe, PC

(57) ABSTRACT

The invention relates to a method for establishing an index for a given cancer grade. The method includes profiling glycan distribution pattern of a reference cancer cell sample; adsorbing the profiled reference cancer cell sample with adsorbents; measuring the amount of the adsorbents adhering onto the profiled reference cancer cell sample; and acquiring reference correlations between the glycan distribution pattern of the reference cancer cell sample and the amount of the adsorbents adhering onto the profiled reference cancer cell sample to form the index of the given cancer grade. An index for a given cancer grade and a method for grading cancer of a test cell sample are also provided.

8 Claims, 12 Drawing Sheets

METHOD FOR CANCER GRADING

TECHNICAL FIELD

The present disclosure relates to cancer diagnosis. Particularly, the present disclosure relates to a method for cancer grading.

DISCUSSION OF THE BACKGROUND

At present, pathologists are responsible for the diagnosis of disease. Hematoxylin-eosin (H&E) stain and immunohistochemistry (IHC) are routine methods applied.

For example, a method of conventional diagnosis of colon cancer employs the colonoscopy or sigmoidoscopy for the detection of lesions and solid tumors. A biopsy is most frequently utilized for diagnosing the degree of malignancy of cancer, and tissue sections taken from the polyp or solid tumor are subjected to H&E staining or IHC staining Unfortunately, making a precisely histopathological examination and reasonable grading cancer and early cancer detection are quite hard. The possible factors include the counting percentage of glandule formation of the detection area and determining the level of degree of the morphology differentiation among well-differentiated benign tissue, precancerous, and malignant tissue at early stage.

Cancer grading of a tissue section is based on not only morphological examination of the tissue section and the percentage of glandule formation in the tissue section, but also the result of cancer grading must be confirmed consistently by three pathologists at least. The possibility of false-negative or false-positive results is still high due to errors caused by artificial operations, detection limit of instrument, and improper pathological examination from individual pathologist's diagnosis. However, the result of cancer grading would affect the follow-up therapy strategies for cancer patients.

SUMMARY

A method of fast diagnosis and high reliability for cancer grading is crucial, especially for diagnosing precancerous tissues and malignant tissues at early stage.

The present disclosure provides a method for establishing an index of a given cancer grade, comprising:

providing a reference cancer cell sample, wherein the reference cancer cell sample has the given cancer grade and comprises glycan chains anchored on the surface of the reference cancer cell sample;

providing a first adsorbent and a second adsorbent, wherein the carbon number of the first adsorbent and the second adsorbent is from 20 to 46, and the carbon number of the first adsorbent is less than that of the second adsorbent;

profiling glycan distribution pattern of the glycan chains anchored on the surface of the reference cancer cell sample;

adsorbing the profiled reference cancer cell sample with the first adsorbent and the second adsorbent, respectively;

measuring the amount of the first adsorbent adhering onto the profiled reference cancer cell sample and measuring the amount of the second adsorbent adhering onto the profiled reference cancer cell sample, respectively; and acquiring a first reference correlation between the glycan distribution pattern of the reference cancer cell sample and the amount of the first adsorbent adhering onto the profiled reference cancer cell sample; acquiring a second reference correlation between the glycan distribution pattern of the reference cancer cell sample and the amount of the second adsorbent adhering onto the profiled reference cancer cell sample, wherein the first reference correlation and the second reference correlation form the index of the given cancer grade.

The present disclosure also provides an index of a given cancer grade, which is established by the method as described above.

The present disclosure also provides a method for grading cancer of a test cell sample, comprising:

providing the test cell sample, wherein the test cell sample comprises glycan chains anchored on the surface of the test sample;

providing a first adsorbent and a second adsorbent, wherein the carbon number of the first adsorbent and the second adsorbent is between 20 and 46, and the carbon number of the first adsorbent is less than that of the second adsorbent;

profiling glycan distribution pattern of the glycan chains anchored on the surface of the test cell sample;

adsorbing the profiled test cell sample with the first adsorbent and the second adsorbent, respectively;

measuring the amount of the first adsorbent adhering onto the profiled test cell sample and measuring the amount of the second adsorbent adhering onto the profiled test cell sample, respectively;

acquiring a first test correlation between the glycan distribution pattern of the test cell sample and the amount of the first adsorbent adhering onto the profiled test cell sample; acquiring a second test correlation between the glycan distribution pattern of the test cell sample and the amount of the second adsorbent adhering onto the determining a cancer grade of the test cell sample by comparing the first test correlation and the second test correlation with the index of the given cancer grade as described above.

The foregoing has outlined the rather broadly features and technical advantages of the present disclosure in order that the detailed description of the disclosure that follows may be better understood. Additional features and technical advantages of the disclosure are described hereinafter, and form the subject of the claims of the disclosure. It should be appreciated by those skilled in the art that the concepts and specific embodiments disclosed may be utilized as a basis for modifying or designing other structures, or processes, for carrying out the purposes of the present disclosure. It should also be realized by those skilled in the art that such equivalent constructions do not depart from the spirit or scope of the disclosure as set forth in the appended claims.

DETAILED DESCRIPTION

Figure 1A:
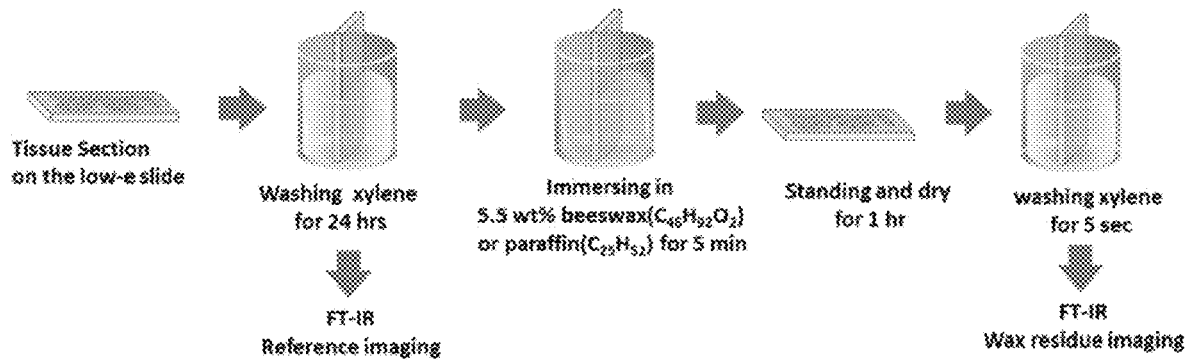
FIGS. 1A-1B shows the procedures of acid-catalyzed hydrolysis (ach) (FIG. 1B) and wax physisorption kinetics (WPK) coupled with FTIR imaging (FIG. 1A) as illustrated in Example 1.

Embodiments, or examples, of the disclosure illustrated in the drawings are now described using specific language. It shall be understood that no limitation of the scope of the disclosure is hereby intended. Any alteration or modification of the described embodiments, and any further applications of principles described in this document, are to be considered as normally occurring to one of ordinary skill in the art to which the disclosure relates.

It shall be understood that, although the terms first, second, third, etc. may be used herein to describe various elements, these elements are not limited by these terms. Rather, these terms are merely used to distinguish one element from another element. Thus, a first element discussed below could be termed a second element without departing from the teachings of the present inventive concept.

The terminology used herein is for the purpose of describing particular example embodiments only and is not intended to be limited to the present inventive concept. As used herein, the singular forms "a," "an" and "the" are intended to include the plural forms as well, unless the context clearly indicates otherwise. It shall be further understood that the terms "comprises" and "comprising," when used in this specification, point out the presence of stated features, integers, steps, operations, elements, or components, but do not preclude the presence or addition of one or more other features, integers, steps, operations, elements, components, or groups thereof.

The present disclosure provides a method for establishing an index of a given cancer grade, comprising:

providing a reference cancer cell sample, wherein the reference cancer cell sample has the given cancer grade and comprises glycan chains anchored on the surface of the reference cancer cell sample;

providing a first adsorbent and a second adsorbent, wherein the carbon number of the first adsorbent and the second adsorbent is from to 46, and the carbon number of the first adsorbent is less than that of the second adsorbent;

profiling glycan distribution pattern of the glycan chains anchored on the surface of the reference cancer cell sample;

adsorbing the profiled reference cancer cell sample with the first adsorbent and the second adsorbent, respectively;

measuring the amount of the first adsorbent adhering onto the profiled reference cancer cell sample and measuring the amount of the second adsorbent adhering onto the profiled reference cancer cell sample, respectively; and acquiring a first reference correlation between the glycan distribution pattern of the reference cancer cell sample and the amount of the first adsorbent adhering onto the profiled reference cancer cell sample; acquiring a second reference correlation between the glycan distribution pattern of the reference cancer cell sample and the amount of the second adsorbent adhering onto the profiled reference cancer cell sample, wherein the first reference correlation and the second reference correlation form the index of the given cancer grade.

As used herein, the term "a cancer grade" describes the level or degree of abnormality for cancer cells and tissues as compared with normal cells and normal tissues. As used herein, the term "a given cancer grade" refers to a cancer grade which is examined and defined according to the result of current medical examinations in pathology.

As used herein, the term "an index" refers to a marker representing a specific cancer grade. The index according to the present disclosure is helpful to provide an objective clinic indicator representing the cancer grade.

As used herein, the term "a reference cancer cell sample" refers to a sample of cancer cells at a given cancer grade defined with current medical examinations. The cancer grade of the reference cancer cell sample is preferably examined or defined by practitioners skilled in this field and is based on a consensus. For example, the cancer grade of the reference cancer cell sample is determined by cell appearance abnormality under microscope and by deviations in its rate of growth. H&E staining or IHC staining may be also applied for the determination of cancer grade.

The reference cancer cell sample comprises glycan chains anchored on the surface of the reference cancer cell sample. The glycan chains usually link to a protein through glycosylation as glycoprotein. Protein glycosylation is the most common post-translational modification, which is involved in crucial physiological processes, including protein folding and unfolding, cell-cell and cell-matrix interactions, and cellular differentiation. Aberrant glycosylation of protein is strongly related to incomplete synthesis and neo-synthesis of glycan chains, which produces a greater population of branched, shorten or elongated glycan chains of glycoprotein during cancerization development. For example, in colon cancer cells, the length of glycan chains linked to protein anchored on the cell membrane has been demonstrated to increase with the cancer grade. Without intending to be limited by theory, it is believed that the elongation of the glycan chains of glycoproteins represents the cancer grade.

Preferably, the cancer according to the disclosure can be benign, pre-malignant, or malignant solid tumor. The kind of cancer as referred to herein includes, for example, brain cancer, cervical cancer, esophageal cancer, thyroid cancer, small cell lung cancer, non-small cell lung cancer, breast cancer, endometrial cancer, lung cancer, gastric cancer, gallbladder/bile duct cancer, liver cancer, pancreatic cancer, colon cancer, ovarian cancer, choriocarcinoma, uterus body cancer, uterocervical cancer, renal pelvis/ureter cancer, bladder cancer, prostate cancer, renal cancer, neuroendocrine tumor, penis cancer, testicles cancer, fetal adenocarcinoma, Wilms tumor, skin cancer, malignant melanoma, neuroblastoma, osteosarcoma, Ewing's tumor, soft part sarcoma, neuroendocrine tumor or oral cavity cancer. More preferably, the cancer is colon cancer, breast cancer, gastric cancer, cervical cancer, prostate cancer, renal cancer, neuroendocrine tumor or oral cavity cancer.

Preferably, the reference cancer cell sample is one of cell lines of the cancer according to the present disclosure. More preferably, the reference cancer cell sample is a cell line derived from colon cancer, breast cancer, prostate cancer, renal cancer, neuroendocrine tumor or oral cavity cancer.

As used herein, the term "an adsorbent" refer to a reagent which is able to adsorb onto cell surface, especially onto cancer cell surface. Preferably, the adsorbents according to the disclosure adsorb glycan chains anchored on the surface of cancer cells. Without intending to be limited by theory, it is believed that the physisorption between adsorbent and glycan chains is strongly suggested relating to a type of physisorption based on van der Waals force interaction and dipole-induced-dipole interaction. The stronger physisorption is established between the adsorbent and glycan chains, the more amount of adsorbent adhering to the cancer cell surface is observed. Based on the van der Waals force interaction and dipole-induced-dipole interaction, the chain length of the glycan chains is close and similar to that of the adsorbent.

The carbon number of the adsorbent according to the present disclosure is between 20 and 46; preferably is between 20 and 34; more preferably is between 22 and 30. According to the present disclosure, the method comprises providing a first adsorbent and a second adsorbent, and the carbon number of the first adsorbent is less than that of the second adsorbent. In one embodiment of the disclosure, the first adsorbent or the second adsorbent is n-alkane or ester with n-alkyl groups at terminals Preferably, the carbon number of an n-alkane as the first adsorbent or the second adsorbent is 22, 25, 28, 30, 32, or 34, such as n-docosane, n-pentacosane, or n-triacontane. In another aspect, the carbon number of an n-alkyl ester as the first adsorbent or the second adsorbent is between 20 and 46, more preferably, is 22, 25, 28, 30, 32, 34, 36, 38, 40, 42, 44 or 46, such as beeswax ($C_{46}H_{92}O_2$).

In one preferred embodiment of the disclosure, a series of adsorbents with different n-alkyl groups are applied for adsorbing different glycan chains anchored on the surface of the cancer cells. For example, a series of adsorbents with carbon number of 22, 25, 28, and 30 are applied in the method according to the present disclosure.

Preferably, the adsorbent according to the present disclosure is preferably formulated as a solution. Preferably, the concentration of the adsorbent according to the present disclosure is between about 1 wt % and about 10 wt %; preferably between about 2.5 wt % and about 7.5 wt %.

Preferably, the cancer cells according to the present disclosure are fixed on a solid substrate, such as glass slide, metal-coated glass slide or quartz slide. The manner of fixing the cancer cells on the solid substrate is known to practitioners skilled in this field.

The method according to the present disclosure comprises profiling glycan distribution pattern of the glycan chains anchored on the surface of the reference cancer cell sample. As used herein, the term "glycan distribution pattern" refers to a type of glycan chains of a cell sample, preferably, of glycan chains linked to protein anchored on the surface of the cell sample. The glycan distribution pattern includes but is not limited to chain length, the kind of monosaccharide, the number of monosaccharide, and the degree level of glycan branching, hydrophobicity, hydrophilicity or polarizability of the glycan, preferably chain length. The glycan distribution pattern represents a distribution of the glycan chains anchored on the surface of the cell sample rather than any specific glycan chains.

The method according to the present disclosure comprises adsorbing the profiled reference cancer cell sample with the first adsorbent and the second adsorbent, respectively; and measuring the amount of the first adsorbent and the second adsorbent adhering onto the profiled reference cancer cell sample, respectively. In view of the carbon number of n-alkyl group of the first adsorbent is less than that of the second adsorbent; these two adsorbents are able to adsorb glycan chains with different lengths. The physisorption capacity between one adsorbent and one glycan chains anchored on one cell sample, including normal and malignant sample, is dramatically different. If the chain length of alkyl groups of one adsorbent and one glycan chains linked to protein anchored on the surface of one cell sample is close to each other, the physisorption capability is stronger there between and more amount of adsorbent adheres onto the cell sample.

The manner of measuring an amount of one adsorbent adhering onto one cell sample includes but is not limited to the process illustrated in Examples. In one preferred embodiment of the present disclosure, wax physisorption kinetics technique is applied. Briefly, the adsorbent adhering onto one cell sample is subjected to a desorption agent, and an amount of adsorbent adhering onto the cell sample is measured by using Fourier-transform infrared spectroscopy imaging technology. For example, the desorption agent is xylene or hexane.

In some embodiment of the present disclosure, the amount of the second adsorbent adhering onto the profiled reference cancer cell sample is greater than that of the first adsorbent. The greater amount of second adsorbent is found on the profiled reference cancer cell sample due to more population area of longer glycan chains anchored in the cancer cell surface than that of normal cell sample. Rather, relative shorter glycan chains as compared to malignant cell sample are found on the normal cell surface.

The method according to the present disclosure comprises acquiring a first reference correlation between the glycan distribution pattern of the reference cancer cell sample and the amount of the first adsorbent adhering onto the profiled reference cancer cell sample; acquiring a second reference correlation between the glycan distribution pattern of the reference cancer cell sample and the amount of the second adsorbent adhering onto the profiled reference cancer cell sample, wherein the first reference correlation and the second reference correlation form the index of the given cancer grade.

In one embodiment of the present disclosure, the profiling, adsorbing and measuring steps comprise:

conducting a hydrolysis reaction for varied lengths of time to stepwise hydrolyze the glycan chains anchored on the reference cancer cell sample;

adsorbing the reference cancer cell sample hydrolyzed for varied time lengths with the first adsorbent and the second adsorbent, respectively;

measuring the amount of the first adsorbent and the second adsorbent adhering onto the reference cancer cell sample hydrolyzed for varied time lengths, respectively.

The hydrolysis reaction of cell sample is performed to hydrolyze the glycan chains anchored on the surface of the cell sample. By measuring the amount of the first adsorbent adhering onto the cell sample and the second adsorbent adhering onto the cell sample after a series of hydrolysis reactions with varied time lengths, the first reference correlation and the second reference correlation are acquired. In one embodiment of the present disclosure, the hydrolysis reaction adopts acid-catalyzed hydrolysis. The chain length of the glycan chains anchored on the surface of the cell sample is shortened by hydrolysis with increased hydrolysis time. In one embodiment of the present disclosure, the time lengths of hydrolysis reaction are between 0 second and about 15 seconds; preferably between 0 second and about 11 seconds. Preferably, the step size of hydrolysis time is set between about 0.5 second and about 5 seconds; more preferably, between about 1 second and about 2 seconds. In another aspect, a reagent for acid-catalyzed hydrolysis is an inorganic acid. Preferably, the hydrolysis reaction is conducted with the reagent at pH value between about −1 and about 6.5, preferably between about 2 and about 5.

In one preferred embodiment of the present disclosure, the first reference correlation or the second reference correlation is acquired by integrating each infrared absorption band in the mid-IR range of 3000-2800 $cm^{-1}$ of the first or second adsorbent adhering onto the hydrolyzed reference cancer cell sample in the mid-IR range of 3000-2800 $cm^{-1}$ in each hydrolysis reaction.

In another embodiment of the present disclosure, the profiling, adsorbing and measuring steps comprise:

applying a series of bias voltages to the reference cancer cell sample;

adsorbing the reference cancer cell sample with applying the bias voltages with the first adsorbent and the second adsorbent, respectively, and adsorbing the reference cancer cell sample without applying the bias voltages with the first adsorbent and the second adsorbent, respectively;

measuring the amount of the first adsorbent adhering onto the reference cancer cell sample and the second adsorbent adhering onto the reference cancer cell sample with applying bias voltages, and measuring the amount of the first adsorbent adhering onto the reference cancer cell sample and the second adsorbent adhering onto the reference cancer cell sample without applying bias voltages, respectively.

Without intending to be limited by theory, it is believed that when a given bias voltage is applied to a given cell sample fixed on a conductive substrate, extra polarization is induced, especially to the glycan chains of the cell surface of the given cell sample. The glycan distribution pattern of the given cell sample at specific cancer grade shows a maximum amount of adsorbent residue at specific bias voltage, called characteristic induced maximum membrane polarization, and induced polarization profile when applied with stepwise increasing bias voltages. Furthermore, the induced polarization is proportional and correlated to infrared absorbance in the mid-IR spectral range of 3000-2800 $cm^{-1}$ of the amount of the adsorbent adhering onto the cell sample. Before reaching characteristic maximum polarization of the cell sample, the physisorption capability is getting stronger between the adsorbent and glycan chains adhering onto the cell sample. Afterward the physisorption capacity is decreasing when the bias voltage applied is greater than that of the characteristic maximum polarization of the cell sample. In one embodiment of the present disclosure, a series of bias voltages are applied in stepwise increase. Each physisorption capacity is determined by measuring infrared absorbance in the range of 3000-2800 $cm^{-1}$ of each adsorbent adhering onto the cell sample with applying each of a series of bias voltages in stepwise increase. Moreover, the breakdown voltage is determined by the amount of the adsorbent adhering onto the cell sample as a given bias voltage being applied is the same as that of the cell sample without applying bias voltage. The physisorption capacity of a given cell sample can be utilized to elaborate on the level of altered glycosylation of glycoprotein and the cancer grade eventually. In one embodiment of the present disclosure, the breakdown bias voltages are determined by comparing the amount of adsorbent adhering onto the cell sample with that of the cell sample without applying bias voltage.

Preferably, the bias voltage is between about 0 V and about 500 V; more preferably between about 0 V and about 300 V; still more preferably between about 0 V and about 200 V. A series of the bias voltage is applied to the cell sample with a voltage increase in 5 V, 10 V or 20 V.

The manner of applying the bias voltages includes but is not limited to the process illustrated in Examples. The strength of electric field is generated by applying a positive bias voltage and ground to the cell samples fixed on a conductive substrate and dummy conductive substrate, respectively. For example, the distance between the two electrodes was set to 5 mm, still more preferably between about 1 mm and about 20 mm and even without grounding electrode.

The first and second correlation reference correlation between the glycan distribution pattern of the reference cancer cell sample profiled by bias voltages and the amount of the first and second adsorbent adhering onto the profiled reference cancer cell sample is acquired.

In one preferred embodiment of the present disclosure, a control assay is included. The method further comprises:

providing a normal cell sample, wherein the normal cell sample comprises intrinsic glycan chains anchored on the surface of the normal cell sample;

profiling glycan distribution pattern of the glycan chains anchored on the surface of the normal cell sample;

adsorbing the profiled normal cell sample with the first adsorbent and the second adsorbent, respectively;

measuring the amount of the first adsorbent adhering onto the profiled normal cell sample and measuring the amount of the second adsorbent adhering onto the profiled normal cell sample, respectively; and acquiring a first control correlation between the glycan distribution pattern of the normal cell sample and the amount of the first adsorbent adhering onto the profiled normal cell sample; acquiring a second control correlation between the glycan distribution pattern of the normal cell sample and the amount of a second adsorbent adhering onto the profiled normal cell sample, respectively.

Preferably, the glycan distribution pattern of the normal cell sample and that of the reference cancer cell sample are different. The manners of performing profiling, adsorbing, measuring and acquiring for the control assay are similar to the description of the reference cancer cell sample at the given cancer grade as described above.

In one example of the present disclosure, human normal colon fibroblast (CCD-18Co), human colon cancer cell lines (SW-1116, SW-480, SW403, LoVo, HT-29), human colon tissue sections, and human oral cavity cancer cell lines (SCC-15, SCC-25, OC-2, OC-3 and OEC-M1) are examined by utilizing acid-catalyzed hydrolysis (ach) coupled with wax physisorption kinetics (ach-WPK) and FTIR imaging. The temporal profile of the amount of each adsorbent adhering onto each cell sample surface is depicted during ach-WPK processes. The maximum amount of the adsorbent adhering onto the cell samples at higher cancer grades occurs at longer hydrolysis time than that at lower cancer grades. On the other hand, the amount of the adsorbent adhering onto tissue section sample of benign tumor or normal fibroblast cells shows an exponential decreasing as increasing hydrolysis time. Moreover, higher grade malignant colon tumor may exhibit two or more adhering maximums of the Paraplast adsorbent (or n-pentacosane) during hydrolysis reactions, indicating that several cancer grades developed within the malignant tumor. Consequently, the hydrolysis time at the maximum amount of the adsorbent adhering on the cell sample can be utilized to establish the index of the given cancer grade.

In one example of the present disclosure, the correlation between breakdown bias voltage or maximum induced membrane polarization and cancer grade of oral cavity cancer is established based on physisorption capability between the cell sample with applying the bias voltage and the amount of adsorbent residue adhering on the oral cavity cancer sample at different cancer grades.

The relative amount of Paraplast (or n-pentacosane) or beeswax ($C_{46}H_{92}O_2$) adhering onto the surface of oral cavity cancer cell samples fixed on a conductive substrate presents a quasi-Gaussian distribution as applying bias voltage in stepwise increase, and the bias voltage at maximum amount of adsorbent adhering is found at 30 V, 30 V, 70 V, 50 V and 70 V for oral cavity cancer cell lines of SCC-25, SCC-15, OC-2, OC-3, and OEC-M1, respectively. Moreover, the breakdown bias voltage for SCC-25, SCC-15, OC-2, OC-3, and OEC-M1 cells, is 85 V, 90 V, 165 V, 167 V, and 183 V, respectively. The consequent result is consistent with pathological cancer grading for oral cavity cancer cells.

The present disclosure also provides an index of a given cancer grade, which is established by the method as described above. As used herein, the term "an index" refers to a marker representing a specific condition. The index according to the invention is helpful to provide an objective clinic value representing the cancer grade for a given sample. Preferably, the index is utilized for grading a given cancer grade of sample. More preferably, the index is based on the infrared absorbance ratio of the amount of the first adsorbent to the second adsorbent adhering onto the given sample.

Preferably, an index group is provided comprising a plurality of the indices of different cancer grades as described above. Preferably, the indices of every cancer grade for a given cancer are established.

The present disclosure still provides a method for grading cancer of a test cell sample, comprising:

providing the test cell sample, wherein the test cell sample comprises glycan chains anchored on the surface of the test cell sample;

providing a first adsorbent and a second adsorbent, wherein the carbon number of the first adsorbent and the second adsorbent is from 20 to 46, and the carbon number of the first adsorbent is less than that of the second adsorbent;

profiling glycan distribution pattern of the glycan chains anchored on the surface of the test cell sample;

adsorbing the profiled test cell sample with the first adsorbent and the second adsorbent, respectively;

measuring the amount of the first adsorbent adhering onto the profiled test cell sample and measuring the amount of the second adsorbent adhering onto the profiled test cell sample, respectively;

acquiring a first test correlation between the glycan distribution pattern of the test cell sample and the amount of the first adsorbent adhering onto the profiled test cell sample;

acquiring a second test correlation between the glycan distribution pattern of the test cell sample and the amount of the second adsorbent adhering onto the profiled test cell sample; and determining a cancer grade of the test cell sample by comparing the first test correlation and the second test correlation with the index of the given cancer grade as described above.

As used herein, the term "a test cell sample" refers to a sample at unknown grade of cancer. The test cell sample includes but is not limited to biopsy or tissue derived from a cancer patient. The test cell sample comprises cancer cells. The manners of performing profiling, adsorbing, measuring and acquiring are similar to the description of the reference cancer cell sample as described above.

The cancer grade of the test cell sample is examined by comparing the first test correlation and the second test correlation with the index as described above. If the first test correlation and the second test correlation are similar or identical to the first reference correlation and a second reference correlation, respectively, the cancer grade of the test cell sample is identified as the same as the given cancer grade.

Preferably, the profiling, adsorbing and measuring steps comprise:

conducting a hydrolysis reaction for varied lengths of time to stepwise hydrolyze the glycan chains anchored on the test cell sample;

adsorbing the test cell sample hydrolyzed for varied time lengths with the first adsorbent and the second adsorbent, respectively;

and measuring the amount of the first adsorbent and the second adsorbent adhering onto the test cell sample hydrolyzed for varied time lengths, respectively.

Preferably, by measuring the amount of the first adsorbent adhering onto the test cell sample and the second adsorbent adhering onto the test cell sample hydrolyzed for varied time length, the first test correlation and the second test correlation are acquired.

Preferably, the profiling, adsorbing and measuring steps comprise:

applying a series of bias voltages to the test cell sample; adsorbing the test cell sample with applying the bias voltages with the first adsorbent and the second adsorbent, respectively, and adsorbing the test cell sample without applying the bias voltages with the first adsorbent and the second adsorbent, respectively;

measuring the amount of the first adsorbent adhering onto the test cell sample and the second adsorbent adhering onto the test cell sample with applying bias voltages, and measuring the amount of the first adsorbent adhering onto the test cell sample and the second adsorbent adhering onto the test cell sample without applying bias voltages, respectively.

Preferably, the first and second correlation reference correlation between the glycan distribution pattern of the test cell sample profiled by using bias voltages and the amount of the first and second adsorbent adhering onto the profiled test cell sample is acquired.

The following examples are provided to aid those skilled in the art in practicing the present disclosure.

Example 1

Cancer Cells
Acid-Catalyzed Hydrolysis

Human normal colon fibroblast (CCD-18Co) and colon cancer cell lines (SW-1116, SW-480, SW403, LoVo, HT-29) were fixed on a low-e slide. The cell sample was immersed into 0.001 N $HCl_{(aq)}$ (pH=3) for a given time length. The $HCl_{(aq)}$ was then removed by DI water washing. The sample was dried and ready for the measurement of FTIR imaging.

Wax-Physisorption-Kinetics-Based FTIR Imaging

The tissue sample was immersed into the solvent of dimethylbenzene (Xylene, $C_8H_{10}$) in the range from 53° C. to 62° C. for 24 hours to remove the paraffin-embedded within tissue section, and the infrared spectrum of the sample fixed on the low-e slide was acquired as the spectra background.

The sample was waxed by immersing into the xylene solution with 5.5 wt % beeswax ($C_{46}H_{92}O_2$) or Paraplast (or n-pentacosane) (as adsorbent) for 5 minutes, and then heating sample at 45° C. for 10 minutes to evaporate xylene residue adhering on the sample. The waxed sample was partially dewaxed by using xylene for 5 seconds, and then stayed at room temperature for evaporating xylene completely. The spatially-resolved infrared spectra of the sample were acquired by FTIR imaging system. After deducting the background, the signal represents the amount of adsorbent residue adhering onto sample surface.

Figure 1B:
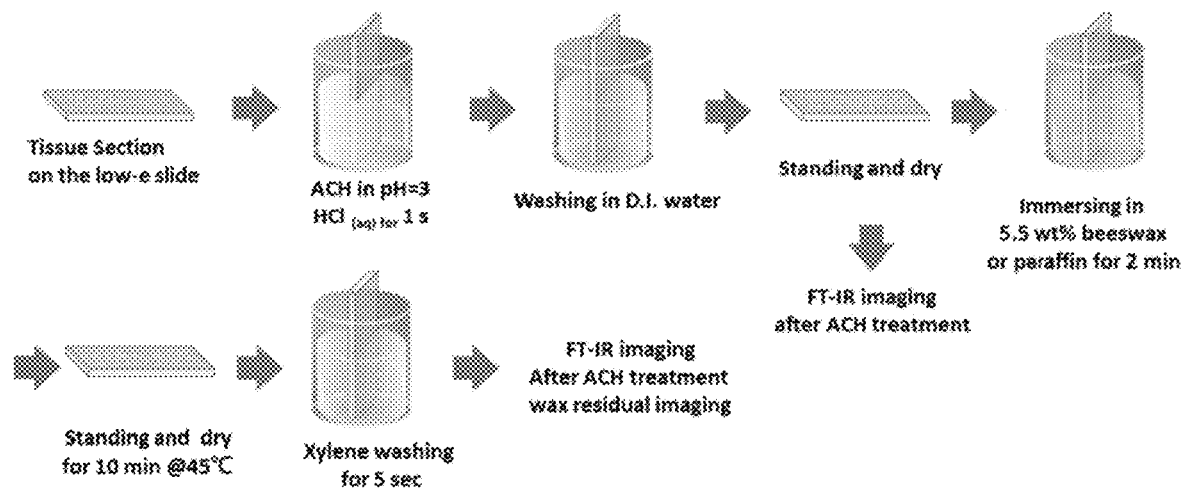

The procedures of acid-catalyzed hydrolysis each) and wax-physisorption-kinetics-based FTIR imaging are shown in FIG. 1.

Figure 2:
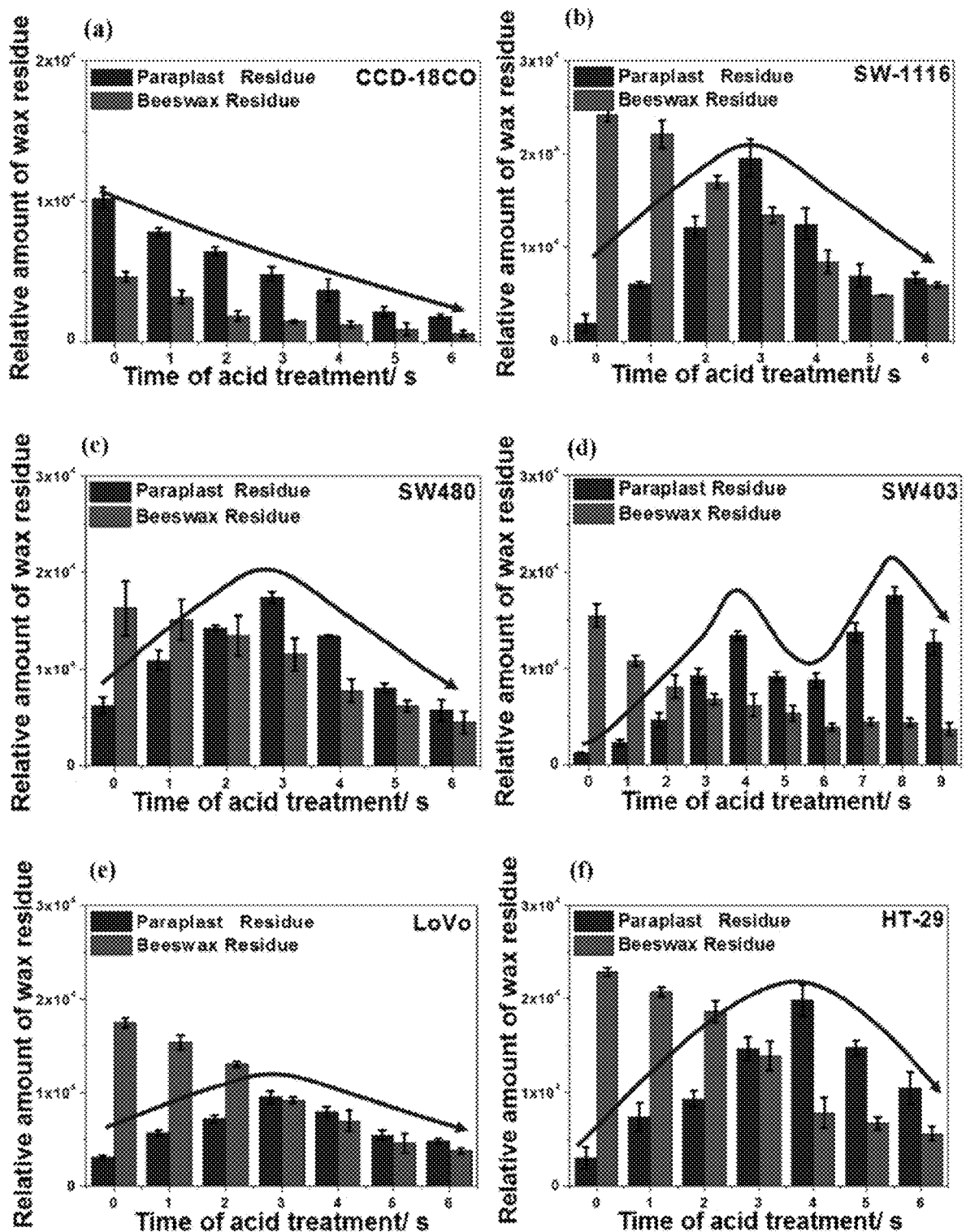
FIG. 2 shows temporal profile of wax physisorption capability between cell samples of CCD-18Co (a), SW-1116 (b), SW-480 (c), SW403 (d), LoVo (e) and HT-29 (f) cells and n-alkanes with different n-alkyl groups after treating with $HCl_{(aq)}$ solution at pH=3 for different time lengths.

The results are shown in FIG. 2. The results of FTIR imaging of ach-WPK for SW-1116, SW-480, SW403, LoVo and HT-29 show an increasing Paraplast (or n-pentacosane) residue, and the maximum amount of Paraplast (or n-pentacosane) residue is observed respectively at $3^{th}$ s, $3^{th}$ $8^{th}$ s, $3^{th}$ s and $4^{th}$ s of hydrolysis.

Figure 3:
FIG. 3 shows spectral images by using WPK-FTIR imaging presenting the distribution of Paraplast (or n-pentacosane) residue and beeswax ($C_{46}H_{92}O_2$) residue adhering onto the surface of the human colon tissue section. Well-differentiated (WD) morphology areas of benign tumor, B1-Bn, B10-Bn, B14-Bn and precancerous area of B10-Pre. Poor-differentiated morphology (PD) areas of tissue malignant areas, B10-Ma and B14-Ma. WD tissue benign area of (a) B1-Bn, (b) B10-Bn, (e) B14-Bn and precancerous area of (c) B10-Pre. The PD tissue malignant area of (c) B10-Ma and (f) B14-Ma. (benign area (Bn), precancerous area (Pre), malignant area (Ma))

As shown in FIG. 3, several regions in the colon tissue section were examined as benign tumor (B1), well-differentiated malignant neoplasm I (B10), poor-differentiated malignant neoplasm II (B14). The tissue section was subjected to processes of WPK-FTIR imaging. Two adsorbents, Paraplast (or n-pentacosane) and beeswax ($C_{46}H_{92}O_2$), were utilized.

The colon tissue section was subjected to ach-WPK and FTIR imaging. The results are shown as from FIGS. 4 to 9. For acquiring the correlation between cancer grade and the level of altered glycosylation of glycoconjugates of a given tissue section, the ach treatment was employed to stepwise de-glycosylate glycan by a series of time lengths of hydrolysis to correlate physisorption capability of hydrolyzed sample with the relative amount of Paraplast (or n-pentacosane) or beeswax ($C_{46}H_{92}O_7$) residue adhering onto tissue section area.

Figure 4:
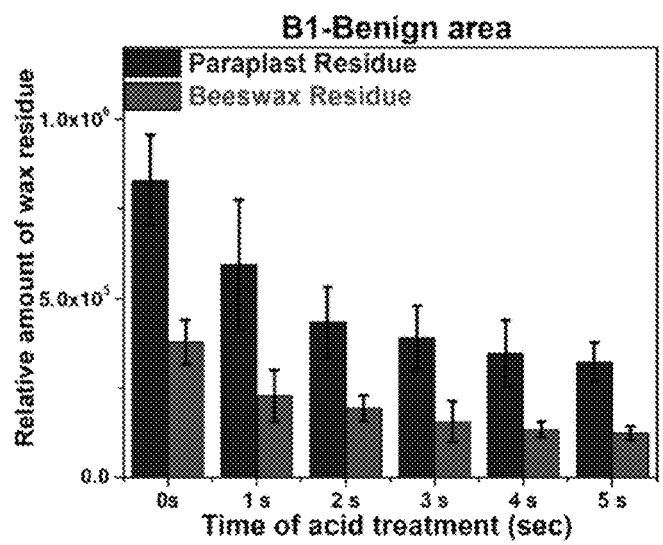
FIG. 4 shows temporal profile of wax residue of the benign tissue section B1-Bn area after hydrolysis for different time lengths.

The temporal profile of adsorbent residue of B1-Bn after hydrolysis for a series time lengths exhibits a single exponential decay of the Paraplast (or n-pentacosane) and beeswax ($C_{46}H_{92}O_2$) residue adhering onto tissue section surface after a series of different hydrolysis time length The ACH-WPK-FTIR spectral images and temporal profile for the amount of wax residue exhibits that less Paraplast (or n-pentacosane) residues while treating a longer time for deglycosylation as shown in FIG. 4, indicating that tissue section is losing the physisorption capability with Paraplast (or n-pentacosane) and beeswax ($C_{46}H_{92}O_2$) while chain length of glycan being shortening after deglycosylation by acid-catalyzed hydrolysis.

Figure 5:
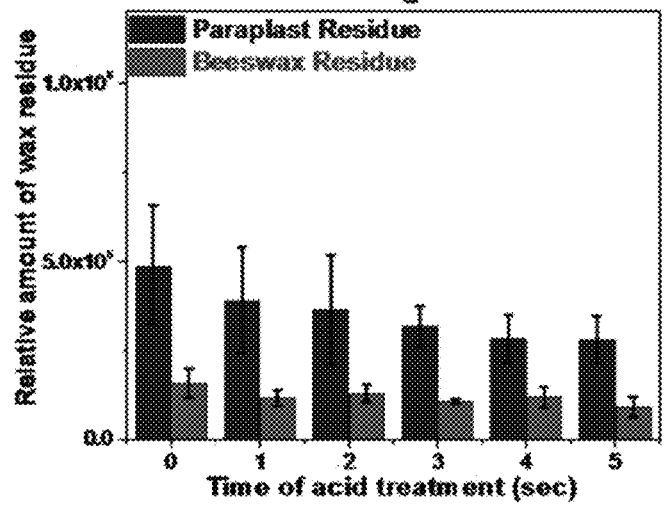
FIG. 5 shows temporal profile of the amount of wax residues adhering onto the B10-Bn area in the benign tissue section after hydrolysis for different time lengths.
Figure 6:
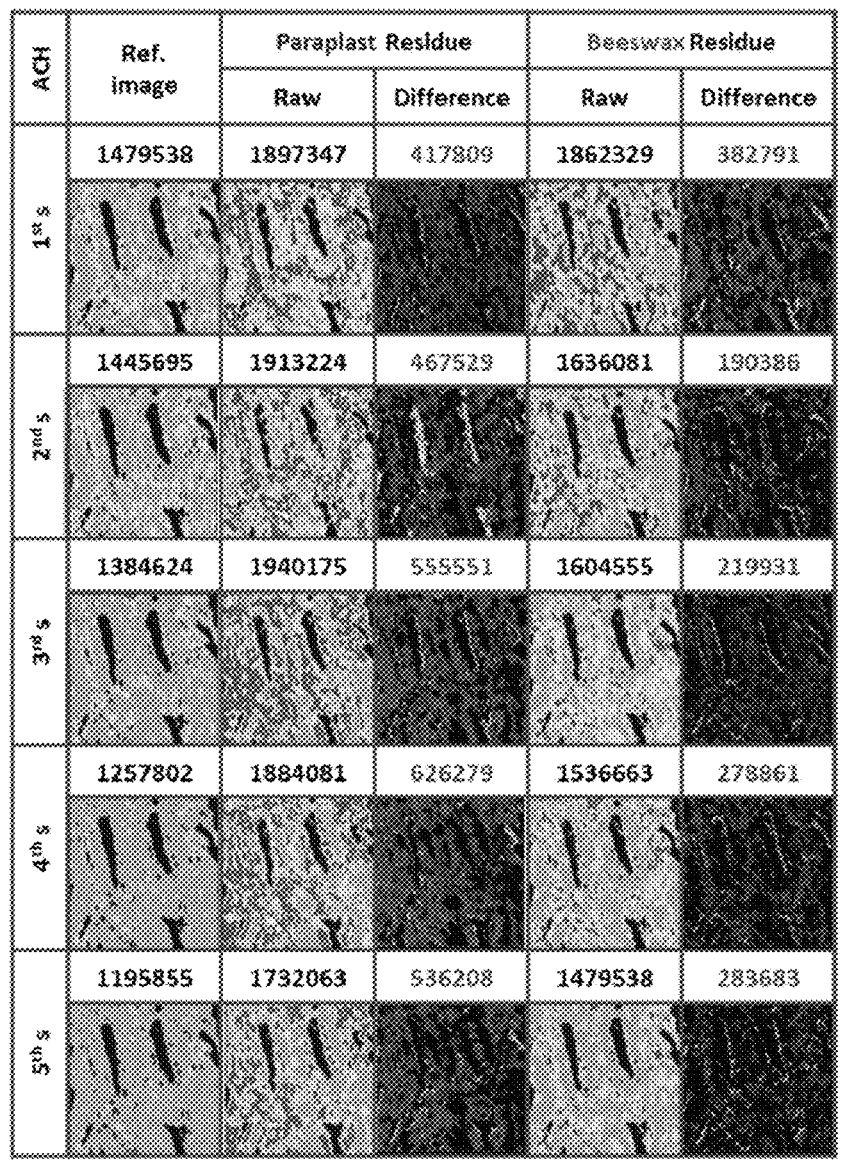
FIG. 6 shows temporal profile of the amount of wax residues adhering onto the precancerous tissue section B10-Pre area after hydrolysis for different time length.
Figure 6:
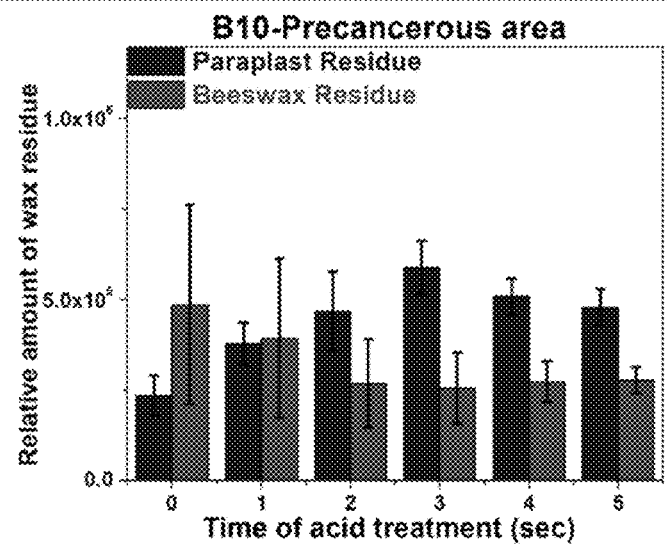
Figure 7:
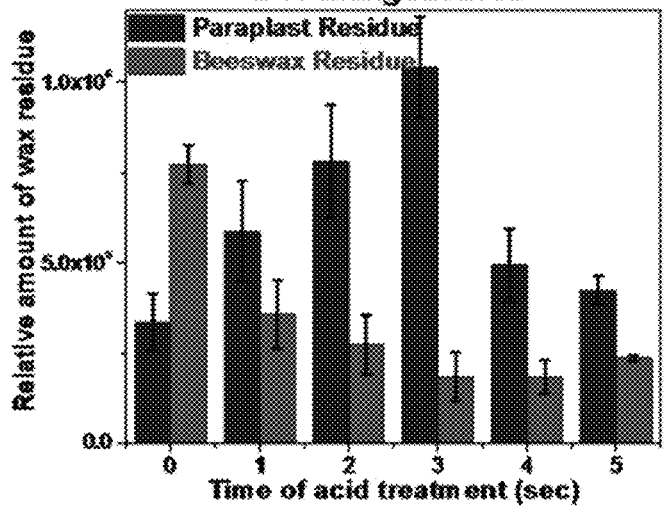
FIG. 7 shows temporal profile of the amount of wax residues adhering onto the malignant tissue section B10-Ma area after hydrolysis for different time lengths.
Figure 8:
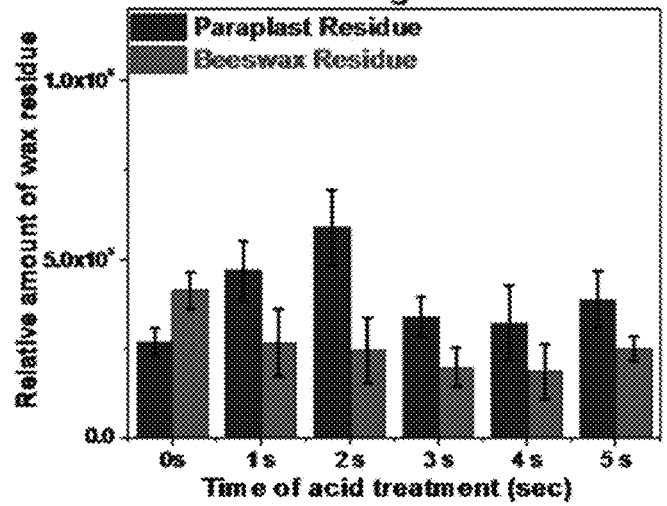
FIG. 8 shows temporal profile of the amount of wax residues adhering onto the benign tissue section B14-Bn area after hydrolysis for different time lengths.
Figure 9:
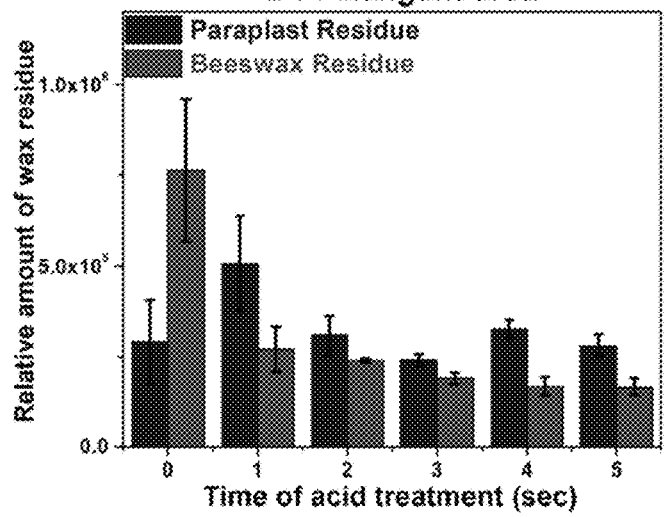
FIG. 9 shows temporal profile of the amount of wax residues adhering onto the malignant tissue section B14-Ma area after hydrolysis for different time lengths.

In the B10-Bn area, the ACH-WPK-FTIR images and temporal profile of Paraplast (or n-pentacosane) residue also show a single exponential decay prior to hydrolysis treatment, but beeswax ($C_{46}H_{92}O_2$) residue does not obviously change as shown in the FIG. 5. The B10-Pre shows a decreasing in the amount of beeswax ($C_{46}H_{92}O_2$) residue during hydrolysis treatment, but increasing amount of Paraplast (or n-pentacosane) residue is observed as shown in the FIG. 6. The ACH-WPK-FTIR spectral images and temporal profile of wax residue adhering onto B10-Ma area show the maximum amount of Paraplast (or n-pentacosane) residue at $3^{th}$ s during hydrolysis, indicating the length of glycan chain was getting shorten during deglycosylation after hydrolysis treatment as shown in the FIG. 7. Hence, the chain length of the rest of hydrolyzed glycan chain is proposed to be similar to the chain length of Paraplast (or n-pentacosane) after hydrolysis for 3 seconds, and a decreasing beeswax ($C_{46}H_{92}O_2$) residue is observed as longer time for hydrolysis because of shortening chain length of glycan chain. Furthermore, the maximum amount of residual Paraplast (or n-pentacosane) is respectively observed after hydrolysis treatment for 2 seconds and a second for benign malignant area in the temporal profile, indicating a high-grade cancer development being progressed in the areas of B14-Bn and B14-Ma as shown in the FIGS. 8 and 9.

Example 2

Oral cancer cell lines SCC-15 (low-grade) and OEC-M1 (high-grade) were subjected to the processes of ACH-WPK coupled with FTIR imaging as described in Example 1, and 0.01 N $HCl_{(aq)}$ (pH=2) was utilized for hydrolyzing glycan chains of cell sample and n-$C_{22}H_{46}$ (n-decothane), n-$C_{25}H_{52}$ (n-pentacosane), n-$C_{28}H_{58}$ (n-octacosane), and beeswax ($C_{46}H_{92}O_2$) were used as glycan adsorbents.

Figure 10:
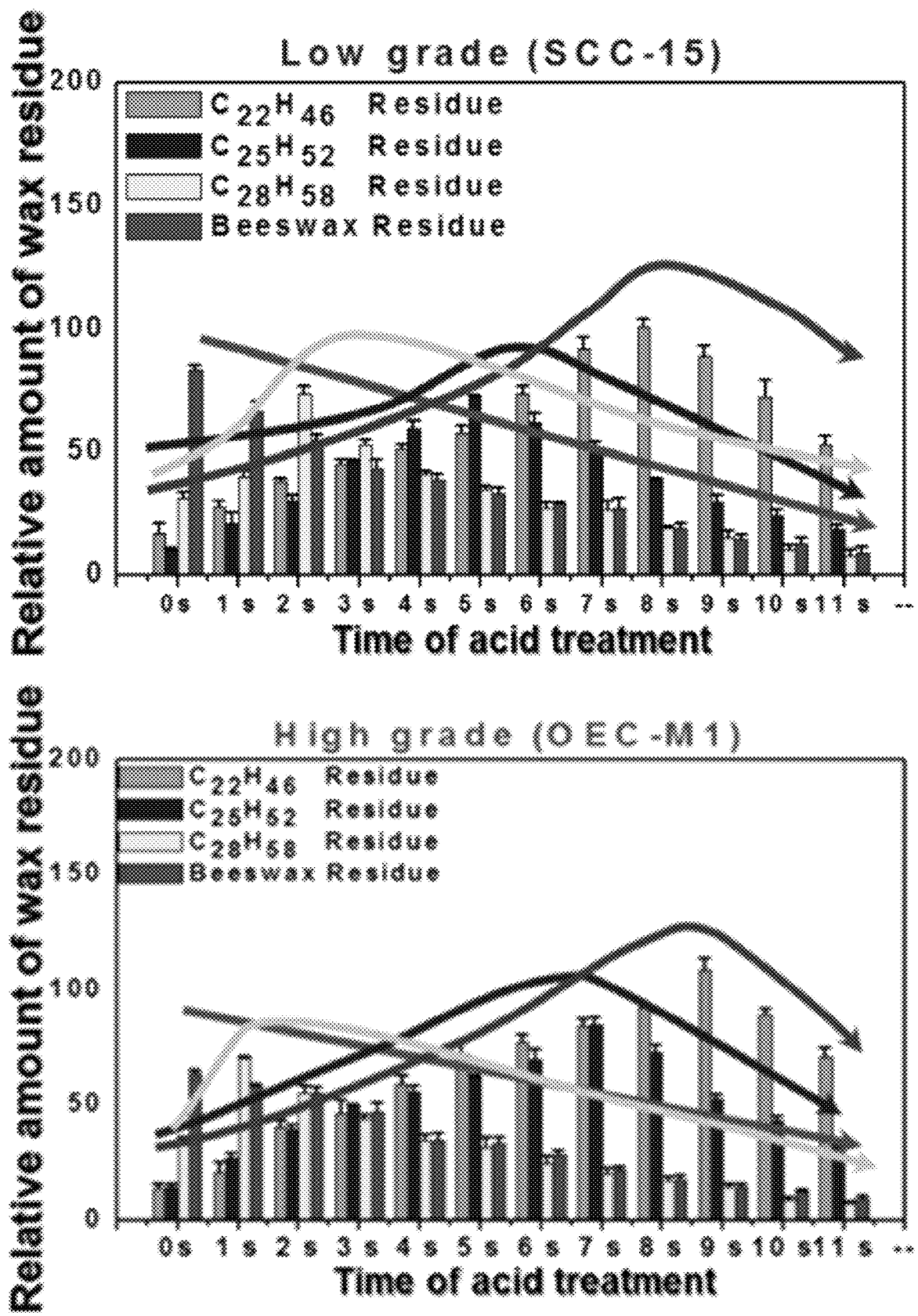
FIG. 10 shows temporal profile of the amount waxes ($n-C_{22}H_{46}$, $n-C_{25}H_{52}$, $n-C_{28}H_{58}$, $n-C_{30}H_{62}$, beeswax ($C_{46}H_{92}O_2$)) residues adhering onto the low-grade sample of oral cavity cancer cells (SCC-15) and the high-grade sample of oral cavity cancer cells (OEC-M1) after hydrolysis for different time lengths.

The results are shown in FIG. 10. ACH-WPK coupled with FTIR imaging is utilized to examine the cancer grade of human oral cavity cancer cells based on the relative amount of n-$C_{22}H_{46}$, n-$C_{25}H_{52}$, n-$C_{28}H_{58}$, and beeswax ($C_{46}H_{92}O_2$) residue adhering onto cell surface. The temporal profile of wax residue reveals that the higher grade of cancer cell sample shows a maximum residue amount of n-alkane adsorbent with shorter n-alkyl chain length after longer time length hydrolysis.

Example 3

Oral cavity cancer cell lines of OEC-M1, SCC-15, SCC-25 OC-2 and OC-3 were fixed on low-e slides.

Wax-Physisorption-Kinetics-Based FTIR Imaging

Figure 11:
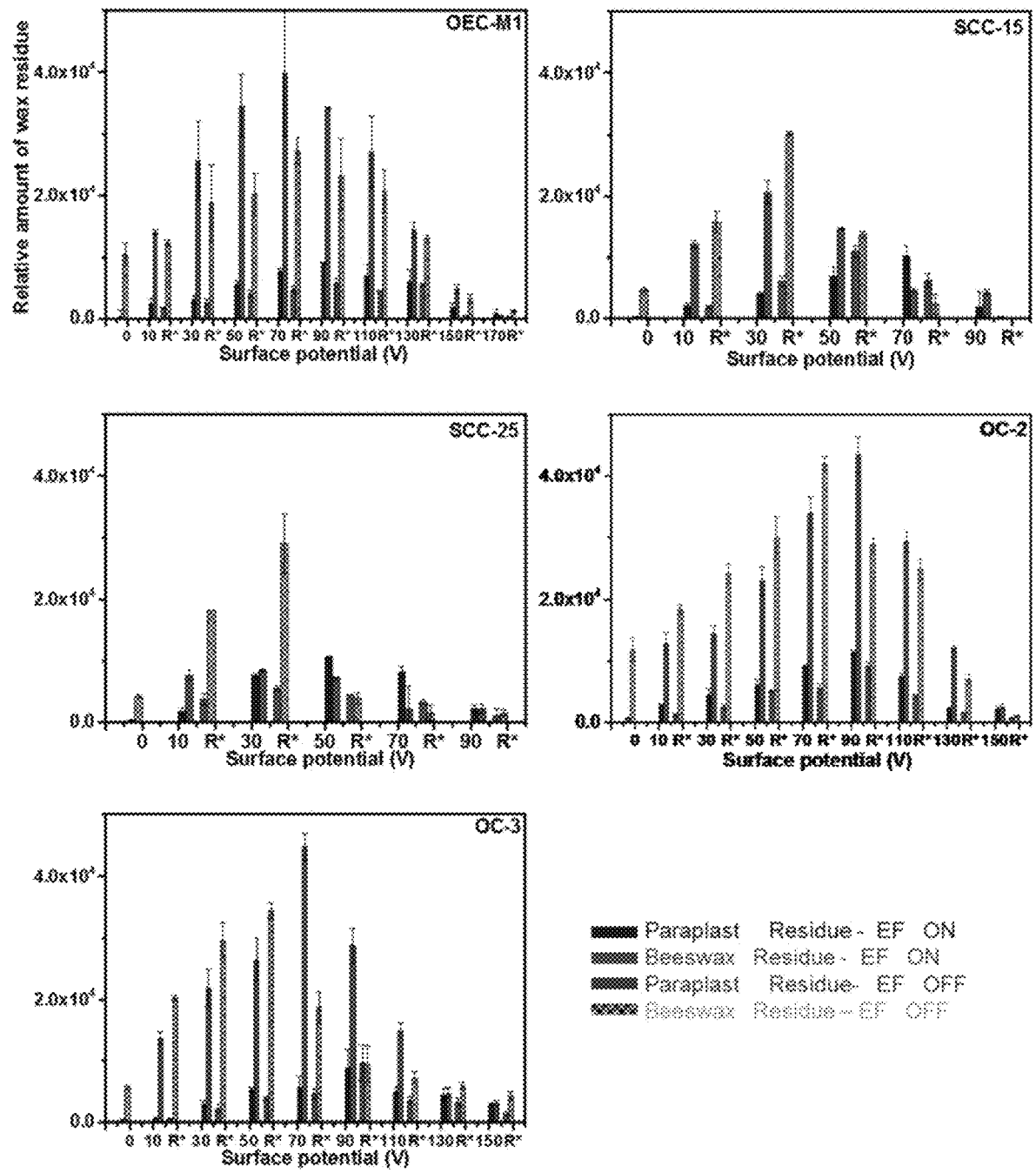
FIG. 11 shows the polarizability profile of the amount of a first and a second adsorbent by using WPK-FTIR imaging of oral cavity cancer cells (OEC-M1, SCC-15, SCC-25, OC-2, OC-3) as applying bias voltages in stepwise increase as illustrated in Example 3.

The sample was cleaned by immersing into xylene solvent for 20 minutes to make sure cell surface free organic is removed, and the FTIR spectrum of the sample was acquired as the spectral background (as shown in FIG. 11).

The sample was waxed by immersing into 5.5 wt % beeswax ($C_{46}H_{92}O_2$) or Paraplast (or n-pentacosane) in xylene solution (as adsorbent) for 2 minutes, and followed up a procedure for evaporating xylene solvent on the sample slide at room temperature for 10 minutes completely. The sample was dewaxed by immersing the sample into pure xylene solvent for 5 seconds (OEC-M1, SCC-15, and SCC-25) or 7 seconds (OC-2 and OC-3), and then stayed at room temperature for evaporating xylene completely. The amount of wax residue adhering onto the cell sample was correlated to the absorbance of residual wax by integrating the area beneath the absorption curve in the spectral range of 3000-2800 cm after subtracting the absorbance of the cell sample before waxing.

Stepwise Increasing Bias Voltages

Bias voltage was applied externally to the sample fixed on a conductive slide, and a given bias-voltage-applied sample was subjected to the procedures of WPK coupled with FUR imaging as described above.

Next, the applying bias voltage externally was released from the sample, and the sample was subjected to the procedures of WPK coupled with FTIR imaging, again (R* is used to stand for the procedure of releasing voltage).

The bias voltages were externally applied to cell samples of oral cavity cancer cell lines from 10 V to 170 V (OEC-M1), 90 V (SCC-15 and SCC-25) or 150 V (OC-2 and OC-3) with voltage step size of 20 V.

The results are shown as in FIG. 11, The result of bias-voltage-assisted WPK shows that the physisorption capability between wax adsorbent and cell sample is enhanced by externally applying a bias voltage. The maximum induced membrane polarizability defined as maximum residual wax adhering onto cell sample at a specific voltage for a given cancer grade of cell sample is also shown in the externally applying voltage range. The cell sample of cancer cell lines exhibit dramatically decrease in physisorption capability of Paraplast (or n-pentacosane) and beeswax ($C_{46}H_{92}O_2$) as a specific voltage being applied, which is define as breakdown voltage of a given cell sample.

Breakdown Bias Voltages

The samples were subjected to a procedure which applying bias voltages by stepwise increasing voltage from 0 V to 300 V with voltage step size from 1 to 10 V as described above for scanning the voltage of the maximum induced membrane polarization and the breakdown of cell sample.

Figure 12:
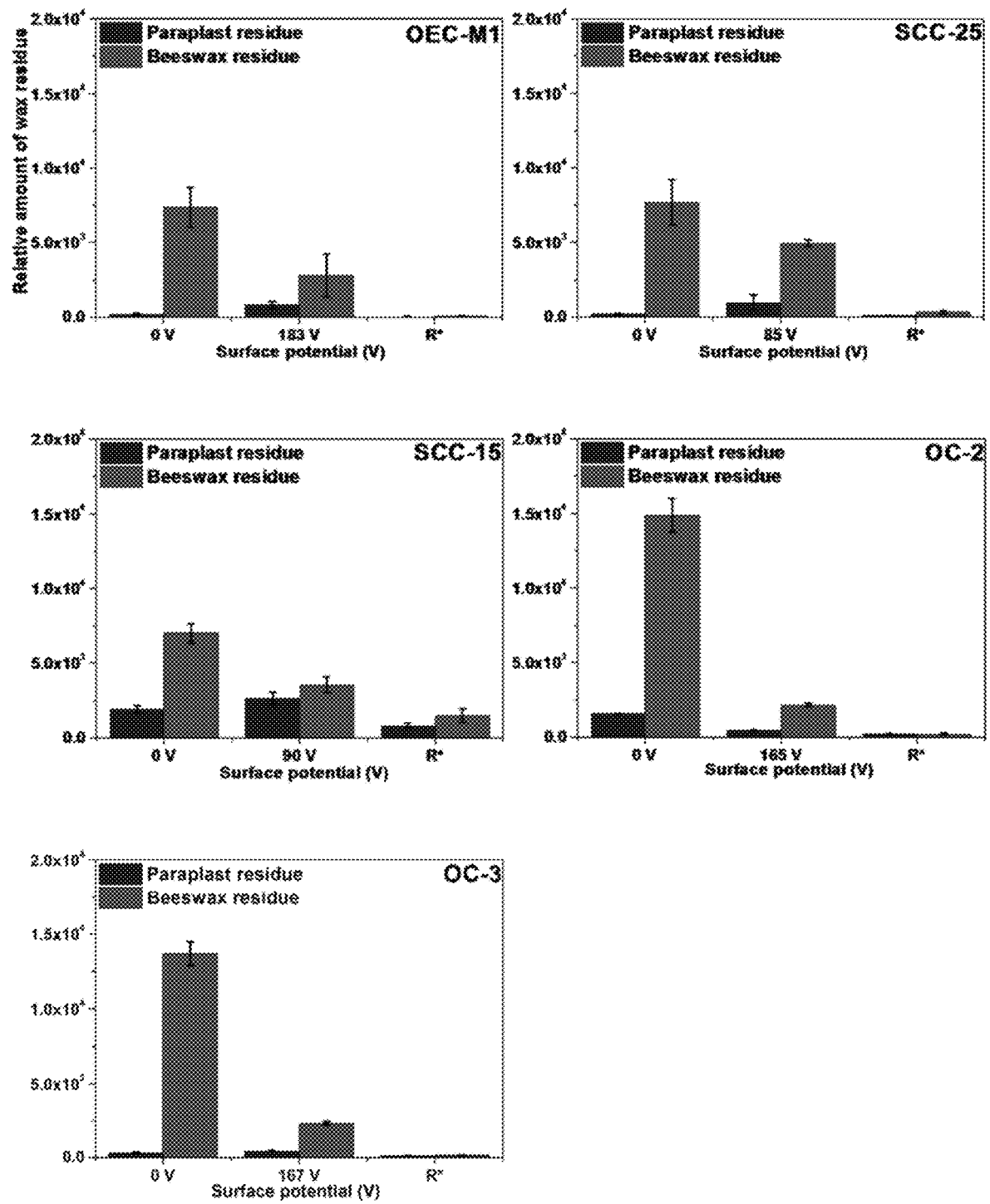
FIG. 12 shows the breakdown bias results of oral cavity cancer cells (OEC-M1, SCC-15, SCC-25, OC-2, OC-3) as applying bias voltages in stepwise increase by using WPK-FTIR imaging as illustrated in Example 3.

The results are shown in FIG. 12. As can be seen, the physisorption capability between cell sample and Paraplast (or n-pentacosane) and beeswax ($C_{46}H_{92}O_2$) is decreased gradually after the breakdown bias being applying at 183 V, 85 V, 90 V, 165 V and 167 V for cancer cells of OEC-M1, SCC-15, SCC-25, OC-2, and OC-3, respectively.

Although the present disclosure and its advantages have been described in detail, it supposes to be fully understood that various changes of operational procedure, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for establishing an index of a given cancer grade, comprising:
   providing a reference cancer cell sample, wherein the reference cancer cell sample is at the given cancer grade and comprises glycan chains of glycoproteins anchored on a surface of the reference cancer cell sample, wherein the reference cancer cell sample is a colon cancer sample;
   providing a first adsorbent and a second adsorbent, wherein a carbon number of the first adsorbent and the second adsorbent is between 20 and 46, and the carbon number of the first adsorbent is lower than that of the second adsorbent;
   profiling glycan distribution pattern of the glycan chains of glycoproteins anchored on the surface of the reference cancer cell sample;
   adsorbing the profiled reference cancer cell sample with the first adsorbent and the second adsorbent, respectively;
   measuring an amount of the first adsorbent adhering onto the profiled reference cancer cell sample and measuring an amount of the second adsorbent adhering onto the profiled reference cancer cell sample, respectively; and
   acquiring a first reference correlation between the glycan distribution pattern of the reference cancer cell sample and the amount of the first adsorbent adhering onto the profiled reference cancer cell sample, and acquiring a second reference correlation between the glycan distribution pattern of the reference cancer cell sample and the amount of the second adsorbent adhering onto the profiled reference cancer cell sample, wherein the first reference correlation and the second reference correlation form the index of the given cancer grade;
   wherein the profiling, adsorbing and measuring steps comprise:
   conducting a hydrolysis reaction for varied time lengths to stepwise hydrolyze the glycan chains of glycoprotein anchored on the reference cancer cell sample;
   adsorbing the reference cancer cell sample hydrolyzed for varied time lengths with the first adsorbent and the second adsorbent, respectively; and
   measuring the amount of the first adsorbent and the second adsorbent adhering onto the reference cancer cell sample hydrolyzed for varied time lengths, respectively;
   wherein the hydrolysis reaction is conducted with a hydrolysis reagent with a pH value higher than 2 to 6.5, and the reference cancer cell sample is immersed in a desorption agent for 24 hours before the profiling, adsorbing and measuring steps.

2. The method according to claim 1, wherein the first adsorbent or the second adsorbent is n-alkane or n-alkyl ester.

3. The method according to claim 1, wherein the profiling, adsorbing and measuring steps comprise:
   applying a series of bias voltages to the reference cancer cell sample;
   adsorbing the reference cancer cell sample with applying the bias voltages with the first adsorbent and the second adsorbent, respectively, and adsorbing the reference cancer cell sample without applying the bias voltages with the first adsorbent and the second adsorbent, respectively;

measuring the amount of the first adsorbent adhering onto the reference cancer cell sample and the second adsorbent adhering onto the reference cancer cell sample with applying bias voltages, and measuring the amount of the first adsorbent adhering onto the reference cancer cell sample and the second adsorbent adhering onto the reference cancer cell sample without applying bias voltages, respectively.

4. The method according to claim 3, wherein the series of bias voltages are from about 0 V to about 500 V.

5. The method according to claim 1, which further comprises:

providing a normal cell sample, wherein the normal cell sample comprises intrinsic glycan chains anchored on surface of the normal cell sample;

profiling glycan distribution pattern of the glycan chains anchored on the surface of the normal cell sample;

adsorbing the profiled normal cell sample with the first adsorbent and the second adsorbent, respectively;

measuring an amount of the first adsorbent and the second adsorbent adhering onto the profiled normal cell sample, respectively; and acquiring a first control correlation between the glycan distribution pattern of the normal cell sample and the amount of the first adsorbent adhering onto the profiled normal cell sample; acquiring a second control correlation between the glycan distribution pattern of the normal cell sample and the amount of a second adsorbent adhering onto the profiled normal cell sample, respectively.

6. A method for grading cancer of a test cell sample, comprising:

providing the test cell sample, wherein the test cell sample comprises glycan chains of glycoproteins anchored on the surface of the test cell sample;

providing a first adsorbent and a second adsorbent, wherein a carbon number of the first adsorbent and the second adsorbent is from between 20 and 46, and the carbon number of the first adsorbent is lower than that of the second adsorbent;

profiling glycan distribution pattern of the glycan chains anchored on the surface of the test cell sample;

adsorbing the profiled test cell sample with the first adsorbent and the second adsorbent, respectively;

measuring an amount of the first adsorbent adhering onto the profiled test cell sample and measuring an amount of the second adsorbent adhering onto the profiled test cell sample, respectively;

acquiring a first test correlation between the glycan distribution pattern of the test cell sample and the amount of the first adsorbent adhering onto the profiled test cell sample; acquiring a second test correlation between the glycan distribution pattern of the test cell sample and the amount of the second adsorbent adhering onto the profiled test cell sample; and determining a cancer grade of the test cell sample by comparing the first test correlation and the second test correlation; wherein the profiling, adsorbing and measuring steps comprise:

conducting a hydrolysis reaction for varied time lengths to stepwise hydrolyze the glycan chains of glycoprotein anchored on the test cell sample:

adsorbing the test cell sample hydrolyzed for varied time lengths with the first adsorbent and the second adsorbent; and wherein the profiling, adsorbing and measuring steps further comprise:

applying a series of bias voltages to the test cell sample;

adsorbing the test cell sample with applying the bias voltages with the first adsorbent and the second adsorbent, respectively, and adsorbing the test cell sample without applying the bias voltages with the first adsorbent and the second adsorbent, respectively;

measuring the amount of the first adsorbent adhering onto the test cell sample and the second adsorbent adhering onto the test cell sample with applying bias voltages, and measuring the amount of the first adsorbent adhering onto the test cell sample and the second adsorbent adhering onto the test cell sample without applying bias voltages, respectively.

7. The method according to claim 6, wherein the first adsorbent or the second adsorbent is n-alkane or n-alkyl ester.

8. The method according to claim 6, wherein the series of bias voltages are from about 0 V to about 500 V.

* * * * *